United States Patent [19]

Koyama et al.

[11] Patent Number: 5,256,330
[45] Date of Patent: Oct. 26, 1993

[54] LACTONE COMPOUND AND COMPOSITION COMPRISING THE SAME

[75] Inventors: Susumu Koyama; Shinichi Saito; Hiromichi Inoue; Masatoshi Fukushima, all of Chiba, Japan

[73] Assignee: Chisso Corporation, Ohsaka, Japan

[21] Appl. No.: 799,074

[22] Filed: Nov. 27, 1991

[30] Foreign Application Priority Data

Nov. 27, 1990 [JP] Japan ................... 2-323710

[51] Int. Cl.$^5$ ................... C09K 19/34; G02F 1/13
[52] U.S. Cl. ................... 252/299.61; 359/103; 252/299.01
[58] Field of Search ............ 252/299.61, 299.01; 549/322, 323; 359/103

[56] References Cited

U.S. PATENT DOCUMENTS

| | | | |
|---|---|---|---|
| 4,909,957 | 3/1990 | Sakaguchi et al. | 252/299.61 |
| 4,973,425 | 11/1990 | Kazuhiko et al. | 252/299.61 |
| 5,026,506 | 6/1991 | Koden et al. | 252/299.61 |
| 5,061,398 | 10/1991 | Takehara et al. | 252/299.61 |

Primary Examiner—Robert L. Stoll
Assistant Examiner—C. Harris
Attorney, Agent, or Firm—Wenderoth, Lind & Ponack

[57] ABSTRACT

A novel lactone compound exhibiting a larger spontaneous polarization value when added to ferroelectric liquid crystal compositions as a basic substance, than those of so far known lactone compounds, and yet having a relatively low viscosity, and a liquid crystal composition comprising the compound, and further a liquid crystal element using the same are provided, the lactone compound being expressed by the formula

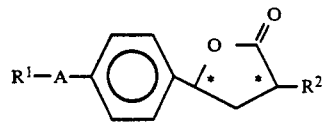

wherein $R^1$ is a linear or branched alkyl group or alkoxy group of 1-15C, $R^2$ is a linear or branched alkyl group of 1-16C, —A— is single bond, 1,4-phenylene group or 1,4-cyclohexylene group and * is an asymmetric carbon atom.

8 Claims, No Drawings

LACTONE COMPOUND AND COMPOSITION COMPRISING THE SAME

BACKGROUND OF THE INVENTION

1. Field of the Invention

This invention relates to a novel optically active compound useful in the fields of liquid crystal display elements and liquid crystal light-switching elements More particularly, it relates to an optically active compound bearing the spontaneous polarization of ferroelectric liquid crystal compositions, a liquid crystal composition containing the compound and a liquid crystal element using the same.

2. Description of the Related Art

At present, TN (Twisted Nematic) display mode has been most broadly employed as a liquid crystal display element. This TN display is provided with many advantages such as low driving voltage, low consumption of electric power, etc. However, as to its response rate, the display element is far inferior to emissive mode display elements such as cathodic ray tube, electroluminescence, plasma display, etc. A new type TN display element having the twist angle increased up to 180° to 270° has also been developed, but its response rate has still been inferior. As described above, although efforts for various improvements have been made, a TN display element having a quick response rate has not yet been realized.

However, in the case of a novel display mode using a ferroelectric liquid crystal, which mode has now been extensively researched, a notable improvement in the response rate has been expected (Clark et al, Applied Phys. lett., 36, 899 (1980)). This display mode utilizes a chiral smectic phase exhibiting a ferroelectricity such as chiral smectic C phase (hereinafter abbreviated to Sc* phase), etc. As liquid crystal phases exhibiting ferroelectricity, there are chiral smectic F, G, H, I, etc., besides Sc* phase.

Many characteristics are required for ferroelectric liquid crystal materials used for ferroelectric liquid crystal display elements for practical use.

Representative examples of the characteristics of ferroelectric liquid crystals are spontaneous polarization (Ps), tilt angle (θ), viscosity (η), liquid crystal phase series, etc.

Molecules in ferroelectric liquid crystals can move only on a cone, and it is also possible to take two states wherein the direction of the major axis of molecules is vertical to the direction of the electric field. The angle formed between the two states has been called "cone angle", and half of the cone angle has been called "tilt angle (θ)". The ferroelectric liquid crystal display mode at present includes mainly two modes: a mode called birefringence mode using two upper and lower polarizing plates, and a guest-host (G·H) mode wherein the polarizing plate is single and a dichroic dyestuff is added to a liquid crystal composition. In order to give the best ratio of brightness to darkness (contrast ratio) of the two states, a tilt angle of 22.5° is required for the birefringence mode, and that of 45° is required for the G·H mode.

Further, since a relationship of τ oc η/Ps exists between the response time (τ) and Ps, η, in order to aim at a high speed response, a material having a large Ps value and a low viscosity is required.

Many characteristics are required for ferroelectric liquid crystal materials practically used for ferroelectric liquid crystal display elements, but it is the present status that no single compound can satisfy such requirements. Accordingly, mixtures of many materials have been provided therefor. Such ferroelectric liquid crystal compositions may be composed of not only liquid crystal compounds, but also non-liquid crystal compounds. Namely, there are a method of composing ferroelectric liquid crystal compositions from only ferroelectric liquid crystal compounds, and a method of mixing compounds or compositions exhibiting tilted smectic phases such as achiral smectic C, F, G, H, I or the like phase (hereinafter abbreviated to Sc or the like phase), as basic substances, with at least one ferroelectric liquid crystal compound or non-liquid crystalline, optically active compound to obtain a resultant exhibiting ferroelectric liquid crystal phase as a whole.

As the basic substances, compounds of various groups exhibiting achiral, smectic liquid crystal phases such as Sc, etc. have been used, but practically, liquid crystal compounds or liquid crystal compositions exhibiting smectic phases within a broad temperature range of low temperatures to room temperature or higher have been used. Among these smectic phases, Sc phase exhibits the highest response rate among ferroelectric liquid crystal phases. For this reason, Sc phase has generally constituted a liquid crystal phase of the basic substances. Examples of the components constituting these smectic C liquid crystal compositions are phenyl benzoates, Schiff's bases, biphenyls, phenylpyridines, phenylpyrimidines, etc.

Further, as compounds which are added to these basic substances to induce ferroelectricity, many compounds have so far been reported.

As the optically active materials which are added to ferroelectric liquid crystal compositions to induce ferroelectricity, the following lactone compounds A, B, C and D have been known:

Compound A:

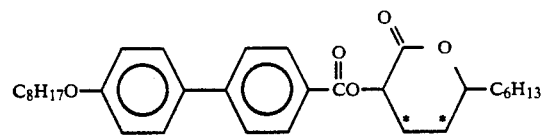

(Preprints of the 15th Japan Liquid Crystal Symposium, 1A05, p. 18 (1989))
(Japanese patent application laid-open No. Hei 1-199959), Compound B:

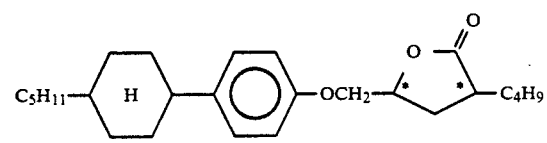

(Preprints of the 15th Japan Liquid Crystal Symposium, 1A11, p. 34),

Compound C:

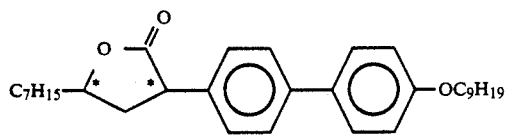

(Preprints of the 16th Japan Liquid Crystal Symposium, 1K117),

Compound D:

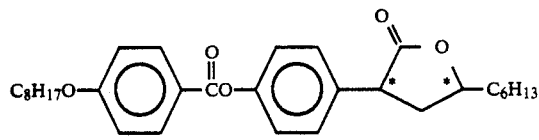

(Preprints of the 16th Japan Liquid Crystal Symposium, 1K116).

These compounds have been described to have a large spontaneous polarization value and to be a superior optically active additive for ferroelectric liquid crystal compositions.

However, compounds A and B each have a linking group such as ester bond, ether bond or oxymethylene bond, between the lactone ring portion and the benzene ring or cyclohexane ring portion. From accumulated data of rotational viscosity in nematic liquid crystal compounds, it is evident that compounds having such a linking group increase viscosity to a large extent. Thus, the above compounds, too, can be said to raise the viscosity of ferroelectric liquid crystal compositions to a large extent.

Further, in the case of compounds C and D, while the five-membered ring lactone and the phenyl group are linked by a single bond, these compounds have a phenyl group linked to α-position of the lactone ring. Although such compounds having a phenyl group linked to α-position of the lactone ring have a relatively large spontaneous polarization value, such a value is not still sufficiently large.

SUMMARY OF THE INVENTION

The object of the present invention is to provide a lactone compound which induces ferroelectricity when added to a ferroelectric liquid crystal composition as a basic substance, thereby obtaining a lactone compound having a larger spontaneous polarization value than those of so far known compounds, and yet having a relatively low viscosity, and a composition containing the lactone compound.

The present inventors have made extensive research in reducing the rotational viscosity of a lactone compound and further increasing the spontaneous polarization value thereof. As a result, they have found that a lactone compound which omits the above linking group, that is a compound expressed by the formula (I), having a phenyl group linked to γ-position of a lactone ring has a larger spontaneous polarization value than that of a compound having a phenyl group linked to α-position of a lactone ring, and yet has a low viscosity. The present invention has thus been achieved.

Namely, the present invention resides in a lactone compound expressed by the formula

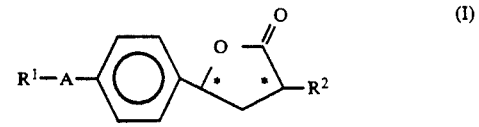

wherein $R^1$ represents a linear or branched alkyl group or alkoxy group of 1 to 15 carbon atoms, $R^2$ represents a linear or branched alkyl group of 1 to 16 carbon atoms, —A— represents a single bond, a 1,4-phenylene group or a 1,4-cyclohexylene group, and * represents an asymmetric carbon atom, and a liquid crystal composition containing the lactone compound, particularly a ferroelectric liquid crystal composition containing the compound, and further a liquid crystal display element containing the same.

DETAILED DESCRIPTION OF PREFERRED EMBODIMENTS

The liquid crystal composition containing the compound of the present invention is preferred to exhibit a nematic or smectic liquid crystal phase.

In the compound expressed by the formula (I), $R^1$ is preferably an alkyl group or alkoxy group of 1 to 12 carbon atoms, more preferably those of 4 to 8 carbon atoms.

$R^2$ is preferably an alkyl group of 1 to 12 carbon atoms, more preferably that of 4 to 8 carbon atoms.

The compound of the formula (I) of the present invention is classified by —A— as follows:

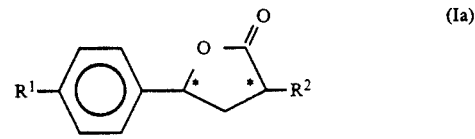

(in the case of —A—=a single bond),

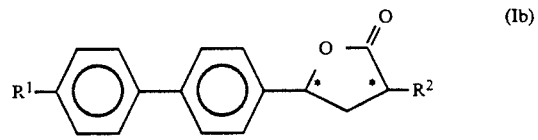

(in the case of —A—=1,4-phenylene), and

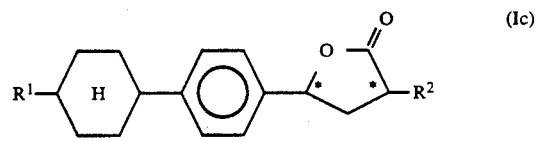

(in the case of —A—=1,4-cyclohexylene).

In the case of —A—=1,4-cyclohexylene, $R^1$ is preferably an alkyl group.

Further, in the compounds of the formula (I), $R^1$ and $R^2$ each may contain one or more methyl or ethyl branches, etc., and in this case, the alkyl group may be optically active.

Herein, concrete examples of optically active groups of $R^1$ and $R^2$ are 1-methylpropyl, 1-methylbutyl, 1-methylpentyl, 1-methylhexyl, 1-methylheptyl, 1-methyloctyl, 1-methylnonyl, 1-methyldecyl, 1-methylundecyl, 1-methyldodecyl, 2-methylbutyl, 3- methylpentyl, 4-methylhexyl, 5-methylheptyl, 6-methyloctyl, 7-methylnonyl, 8-methyldecyl, etc.

Further, when $R^1$ and $R^2$ are each not optically active examples of preferably compounds are as follows:

α-butyl-γ-(4-butylphenyl)-γ-butyrolactone (No. 1)
α-butyl-γ-(4-pentylphenyl)-γ-butyrolactone (No. 2)
α-butyl-γ-(4-hexylphenyl)-γ-butyrolactone (No. 3)
α-butyl-γ-(4-heptylphenyl)-γ-butyrolactone (No. 4)
α-butyl-γ-(4-octylphenyl)-γ-butyrolactone (No. 5)
α-pentyl-γ-(4-butylphenyl)-γ-butyrolactone (No. 6)
α-pentyl-γ-(4-pentylphenyl)-γ-butyrolactone (No. 7)
α-pentyl-γ-(4-hexylphenyl)-γ-butyrolactone (No. 8)
α-pentyl-γ-(4-heptylphenyl)-γ-butyrolactone (No. 9)
α-pentyl-γ-(4-octylphenyl)-γ-butyrolactone (No. 10)
α-hexyl-γ-(4-butylphenyl)-γ-butyrolactone (No. 11)
α-hexyl-γ-(4-pentylphenyl)-γ-butyrolactone (No. 12)
α-hexyl-γ-(4-hexylphenyl)-γ-butyrolactone (No. 13)
α-hexyl-γ-(4-heptylphenyl)-γ-butyrolactone (No. 14)
α-hexyl-γ-(4-octylphenyl)-γ-butyrolactone (No. 15)
heptyl-γ-(4-butylphenyl)-γ-butyrolactone (No. 16)
α-heptyl-γ-(4-pentylphenyl)-γ-butyrolactone (No. 17)
α-heptyl-γ-(4-hexylphenyl)-γ-butyrolactone (No. 18)
α-heptyl-γ-(4-heptylphenyl)-γ-butyrolactone (No. 19)
α-heptyl-γ-(4-octylphenyl)-γ-butyrolactone (No. 20)
α-octyl-γ-(4-butylphenyl)-γ-butyrolactone (No. 21)
α-octyl-γ-(4-pentylphenyl)-γ-butyrolactone (No. 22)
α-octyl-γ-(4-hexylphenyl)-γ-butyrolactone (No. 23)
α-octyl-γ-(4-heptylphenyl)-γ-butyrolactone (No. 24)
α-octyl-γ-(4-octylphenyl)-γ-butyrolactone (No. 25)
α-butyl-γ-(4-butoxyphenyl)-γ-butyrolactone (No. 26)
-α-butyl-γ-(4-pentyloxyphenyl)-γ-butyrolactone (No. 27)
α-butyl-γ-(4-hexyloxyphenyl)-γ-butyrolactone (No. 28)
α-butyl-γ-(4-heptyloxyphenyl)-γ-butyrolactone (No. 29)
α-butyl-γ-(4-octyloxyphenyl)-γ-butyrolactone (No. 30)
α-pentyl-γ-(4-butoxyphenyl)-γ-butyrolactone (No. 31)
α-pentyl-γ-(4-pentyloxyphenyl)-γ-butyrolactone (No. 32)
α-pentyl-γ-(4-hexyloxyphenyl)-γ-butyrolactone (No. 33)
α-pentyl-γ-(4-heptyloxyphenyl)-γ-butyrolactone (No. 34)
α-pentyl-γ-(4-octyloxyphenyl)-γ-butyrolactone (No. 35)
α-hexyl-γ-(4-butoxyphenyl)-γ-butyrolactone (No. 36)
α-hexyl-γ-(4-pentyloxyphenyl)-γ-butyrolactone (No. 37)
α-hexyl-γ-(4-hexyloxyphenyl)-γ-butyrolactone (No. 38)
α-hexyl-γ-(4-heptyloxyphenyl)-γ-butyrolactone (No. 39)
α-hexyl-γ-(4-octyloxyphenyl)-γ-butyrolactone (No. 40)
α-heptyl-γ-(4-butoxyphenyl)-γ-butyrolactone (No. 41)
α-heptyl-γ-(4-pentyloxyphenyl)-γ-butyrolactone (No. 42)
α-heptyl-γ-(4-hexyloxyphenyl)-γ-butyrolactone (No. 43)
α-heptyl-γ-(4-heptyloxyphenyl)-γ-butyrolactone (No. 44)
α-heptyl-γ-(4-octyloxyphenyl)-γ-butyrolactone (No. 45)
α-octyl-γ-(4-butoxyphenyl)-γ-butyrolactone (No. 46)
α-octyl-γ-(4-pentyloxyphenyl)-γ-butyrolactone (No. 47)
α-octyl-γ-(4-hexyloxyphenyl)-γ-butyrolactone (No. 48)
α-octyl-γ-(4-heptyloxyphenyl)-γ-butyrolactone (No. 49)
α-octyl-γ-(4-octyloxyphenyl)-γ-butyrolactone (No. 50)
α-butyl-γ-(4'-butylbiphenyl-4-yl)-γ-butyrolactone (No. 51)
α-butyl-γ-(4'-pentylbiphenyl-4-yl)-γ-butyrolactone (No. 52)
α-butyl-γ-(4'-hexylbiphenyl-4-yl)-γ-butyrolactone (No. 53)
α-butyl-γ-(4'-heptylbiphenyl-4-yl)-γ-butyrolactone (No. 54)
α-butyl-γ-(4'-octylbiphenyl-4-yl)-γ-butyrolactone (No. 55)
α-pentyl-γ-(4'-butylbiphenyl-4-yl)-γ-butyrolactone (No. 56)
α-pentyl-γ-(4'-pentylbiphenyl-4-yl)-γ-butyrolactone (No. 57)
α-pentyl-γ-(4'-hexylbiphenyl-4-yl)-γ-butyrolactone (No. 58)
α-pentyl-γ-(4'-heptylbiphenyl-4-yl)-γ-butyrolactone (No. 59)
α-pentyl-γ-(4'-octylbiphenyl-4-yl)-γ-butyrolactone (No. 60)
α-hexyl-γ-(4'-butylbiphenyl-4-yl)-γ-butyrolactone (No. 61)
α-hexyl-γ-(4'-pentylbiphenyl-4-yl)-γ-butyrolactone (No. 62)
α-hexyl-γ-(4'-hexylbiphenyl-4-yl)-γ-butyrolactone (No. 63)
α-hexyl-γ-(4'-heptylbiphenyl-4-yl)-γ-butyrolactone (No. 64)
α-hexyl-γ-(4'-octylbiphenyl-4-yl)-γ-butyrolactone (No. 65)
α-heptyl-γ-(4'-butylbiphenyl-4-yl)-γ-butyrolactone (No. 66)
α-heptyl-γ-(4-pentylbiphenyl-4-yl)-γ-butyrolactone (No. 67)
α-heptyl-γ-(4'-hexylbiphenyl-4-yl)-γ-butyrolactone (No. 68)
α-heptyl-γ-(4'-heptylbiphenyl-4-yl)-γ-butyrolactone (No. 69)
α-heptyl-γ-(4'-octylbiphenyl-4-yl)-γ-butyrolactone (No. 70)
α-octyl-γ-(4'-butylbiphenyl-4-yl)-γ-butyrolactone (No. 71)
α-octyl-γ-(4'-pentylbiphenyl-4-yl)-γ-butyrolactone (No. 72)
αoctyl-γ-(4'-hexylbiphenyl-4-yl)-γ-butyrolactone (No. 73)
α-octyl-γ-(4'-heptylbiphenyl-4-yl)-γ-butyrolactone (No. 74)
α-octyl-γ-(4'-octylbiphenyl-4-yl)-γ-butyrolactone (No. 75)
α-butyl-γ-(4'-butoxybiphenyl-4-yl)-γ-butyrolactone (No. 76)
α-butyl-γ-(4'-pentyloxybiphenyl-4-yl)-γ-butyrolactone (No. 77)
α-butyl-γ-(4'-hexyloxybiphenyl-4-yl)-γ-butyrolactone (No. 78)
α-butyl-γ-(4'-heptyloxybiphenyl-4-yl)-γ-butyrolactone (No. 79)
α-butyl-γ-(4'-octyloxybiphenyl-4-yl)-γ-butyrolactone (No. 80)
α-pentyl-γ-(4'-butoxybiphenyl-4-yl)-γ-butyrolactone (No. 81)
α-pentyl-γ-(4'-pentyloxybiphenyl-4-yl)-γ-butyrolactone (No. 82)
α-pentyl-γ-(4'-hexyloxybiphenyl-4-yl)-γ-butyrolactone (No. 83)

α-pentyl-γ-(4'-heptyloxybiphenyl-4-yl)-γ-butyrolactone (No. 84)
α-pentyl-γ-(4'-octyloxybiphenyl-4-yl)-γ-butyrolactone (No. 85)
α-hexyl-γ-(4'-butoxybiphenyl-4-yl)-γ-butyrolactone (No. 86)
α-hexyl-γ-(4'-pentyloxybiphenyl-4-yl)-γ-butyrolactone (No. 87)
α-hexyl-γ-(4'-hexyloxybiphenyl-4-yl)-γ-butyrolactone (No. 88)
α-hexyl-γ-(4'-heptyloxybiphenyl-4-yl)-γ-butyrolactone (No. 89)
α-hexyl-γ-(4'-octyloxybiphenyl-4-yl)-γ-butyrolactone (No. 90)
α-heptyl-γ-(4'-butoxybiphenyl-4-yl)-γ-butyrolactone (No. 91)
α-heptyl-γ-(4'-pentyloxybiphenyl-4-yl)-γ-butyrolactone (No. 92)
α-heptyl-γ-(4'-hexyloxybiphenyl-4-yl)-γ-butyrolactone (No. 93)
α-heptyl-γ-(4'-heptyloxybiphenyl-4-yl)-γ-butyrolactone (No. 94)
α-heptyl-γ-(4'-octyloxybiphenyl-4-yl)-γ-butyrolactone (No. 95)
α-octyl-γ-(4'-butoxybiphenyl-4-yl)-γ-butyrolactone (No. 96)
α-octyl-γ-(4'-pentyloxybiphenyl-4-yl)-γ-butyrolactone (No. 97)
α-octyl-γ-(4'-hexyloxybiphenyl-4-yl)-γ-butyrolactone (No. 98)
α-octyl-γ-(4'-heptyloxybiphenyl-4-yl)-γ-butyrolactone (No. 99)
α-octyl-γ-(4'-octyloxybiphenyl-4-yl)-γ-butyrolactone (No. 100)
α-butyl-γ-(4-(4'-butylcyclohexyl)phenyl-γ-butyrolactone (No. 101)
α-butyl-γ-(4-(4'-pentylcyclohexyl)phenyl-γ-butyrolactone (No. 102)
α-butyl-γ-(4-(4'-hexylcyclohexyl)phenyl-γ-butyrolactone (No. 103)
α-butyl-γ-(4-(4'-heptylcyclohexyl)phenyl-γ-butyrolactone (No. 104)
α-butyl-γ-(4-(4'-octylcyclohexyl)phenyl-γ-butyrolactone (No. 105)
α-pentyl-γ-(4-(4'-butylcyclohexyl)phenyl-γ-butyrolactone (No. 106)
α-pentyl-γ-(4-(4'-pentylcyclohexyl)phenyl-γ-butyrolactone (No. 107)
α-pentyl-γ-(4-(4'-hexylcyclohexyl)phenyl-γ-butyrolactone (No. 108)
α-pentyl-γ-(4-(4'-heptylcyclohexyl)phenyl-γ-butyrolactone (No. 109)
α-pentyl-γ-(4-(4'-octylcyclohexyl)phenyl-γ-butyrolactone (No. 110)
α-hexyl-γ-(4-(4'-butylcyclohexyl)phenyl-γ-butyrolactone (No. 111)
α-hexyl-γ-(4-(4'-pentylcyclohexyl)phenyl-γ-butyrolactone (No. 112) (No. 113)
α-hexyl-γ-(4-(4'-heptylcyclohexyl)phenyl-γ-butyrolactone (No. 114)
α-hexyl-γ-(4-(4'-octylcyclohexyl)phenyl-γ-butyrolactone (No. 115)
α-heptyl-γ-(4-(4'-butylcyclohexyl)phenyl-γ-butyrolactone (No 116)
α-heptyl-γ-(4-(4'-pentylcyclohexyl)phenyl-γ-butyrolactone (No 117)
α-heptyl-γ-(4 -(4'-hexylcyclohexyl)phenyl-γ-butyrolactone (No. 118)
α-heptyl-γ-(4-(4'-heptylcyclohexyl)phenyl-γ-butyrolactone (No. 119)
α-heptyl-γ-(4-(4'-octylcyclohexyl)phenyl-γ-butyrolactone (No. 120)
α-octyl-γ-(4-(4'-butylcyclohexyl)phenyl-γ-butyrolactone (No. 121)
α-octyl-γ-(4-(4'-pentylcyclohexyl)phenyl-γ-butyrolactone (No. 122)
α-octyl-γ-(4-(4'-hexylcyclohexyl)phenyl-γ-butyrolactone (No. 123)
α-octyl-γ-(4-(4'-heptylcyclohexyl)phenyl-γ-butyrolactone (No. 124)
α-octyl-γ-(4-(4'-octylcyclohexyl)phenyl-γ-butyrolactone (No. 125)

Further, representative examples of the achiral liquid crystal compounds useful as a component constituting the basic substance capable of inducing ferroelectricity at the time of adding the optically active compound of the present invention are as follows:

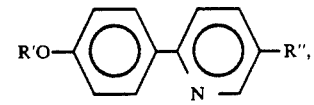

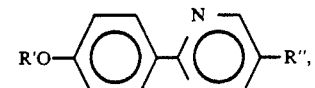

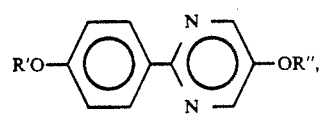

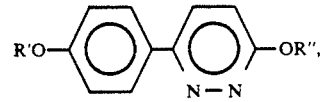

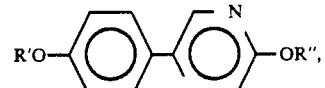

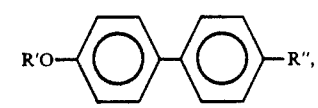

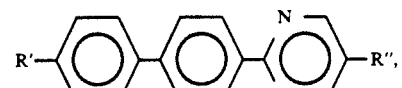

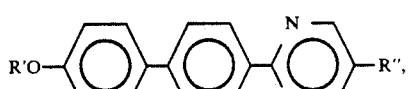

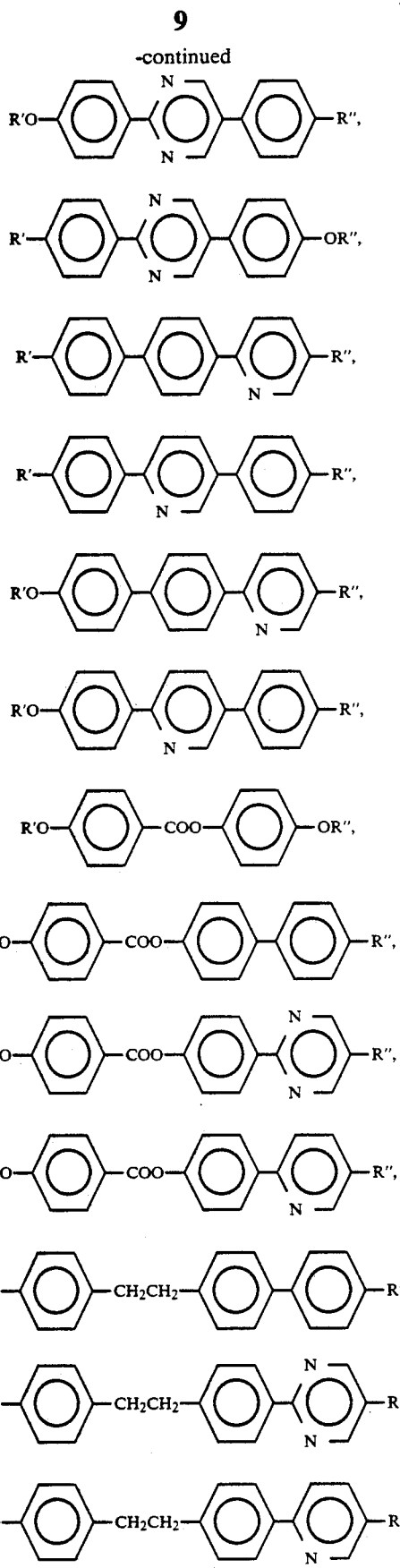

wherein R' and R" each represent an alkyl group or an alkenyl group of 1 to 20 carbon atoms.

Further, in order to derive the dielectric anisotropy into its negative value, it is also possible to add a compound having a partial structure such as the following means:

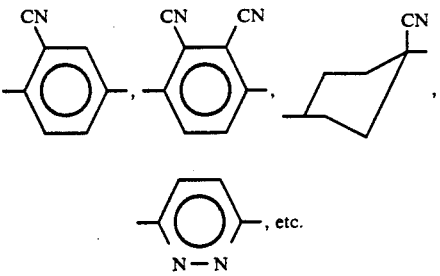

PREPARATION OF THE COMPOUND

The compound of the present invention can be preferably prepared through the following route:

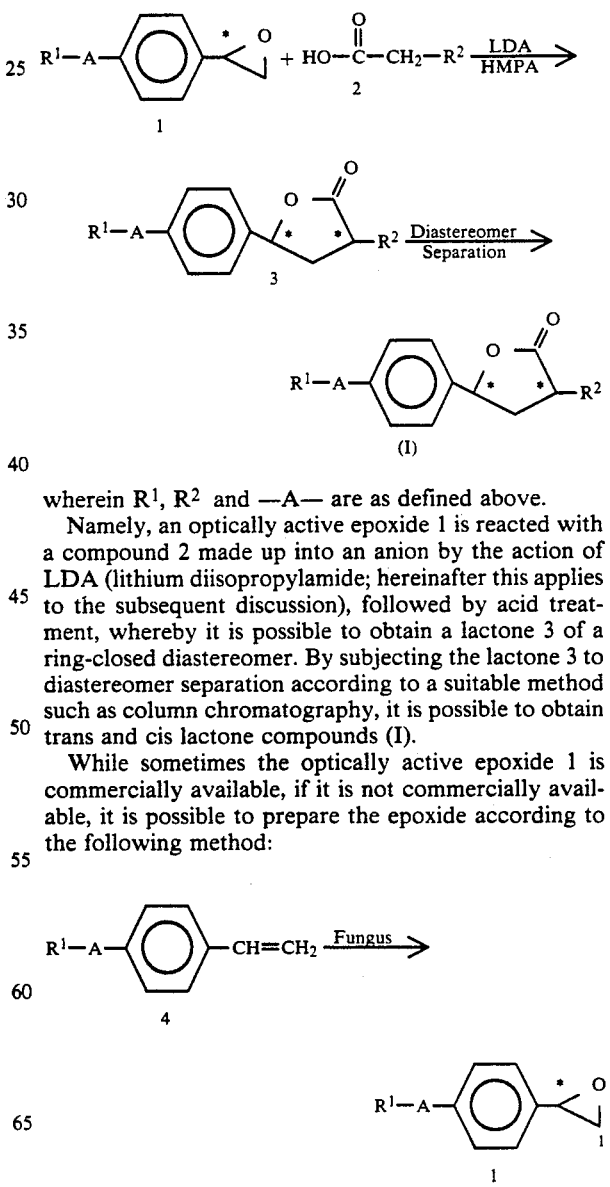

wherein $R^1$, $R^2$ and —A— are as defined above.

Namely, an optically active epoxide 1 is reacted with a compound 2 made up into an anion by the action of LDA (lithium diisopropylamide; hereinafter this applies to the subsequent discussion), followed by acid treatment, whereby it is possible to obtain a lactone 3 of a ring-closed diastereomer. By subjecting the lactone 3 to diastereomer separation according to a suitable method such as column chromatography, it is possible to obtain trans and cis lactone compounds (I).

While sometimes the optically active epoxide 1 is commercially available, if it is not commercially available, it is possible to prepare the epoxide according to the following method:

wherein R¹ and —A— are as defined above.

Namely, by oxidizing the corresponding olefin 4 by means of a microorganism such as fungi, it is possible to prepare the optically active epoxide 1. As fungi useful at that time, there are Nocardia, Corallina, etc.

Further, the compound 1 may also be preferably prepared according to the following process:

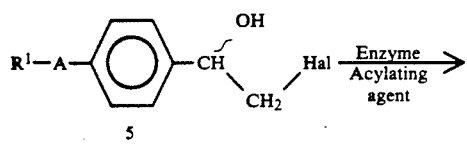
5

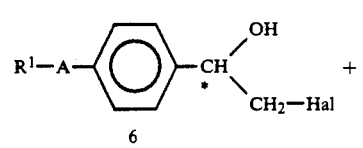
6

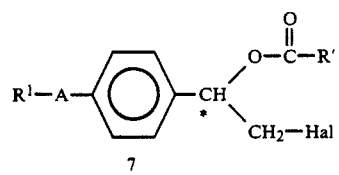
7

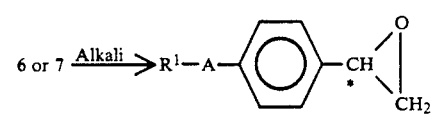
1 wherein R¹ and —A— are as defined above, Hal represents a halogen atom and R' represents an alkyl group such as methyl, ethyl, etc.

Namely, when a halogenated alcohol 5 which a racemic substance is reacted with a suitable acylating agent in the presence of an enzyme and in an organic solvent or an inorganic solvent, it is possible to subject the compound 5 to optical resolution into an optically active alcohol 6 and an optically active ester 7 having an absolute configuration different from that of 6. By treating either one of the compound 6 or the compound 7 with an alkali, it is possible to obtain the epoxide 1.

At that time, as the enzyme preferably used for the optical resolution, there are enzymes originated from Pseudomonas such as lipase Ps made by Amano Seiyaku Co., Ltd., etc.

Further, as the acylating agent preferably used, there are tributyrin, tripropionin, vinyl valerate, etc.

Further, the compound of the present invention may be preferably prepared according to the following method:

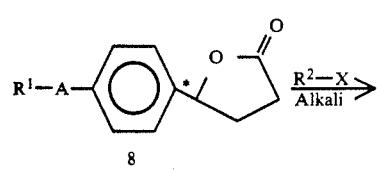
8

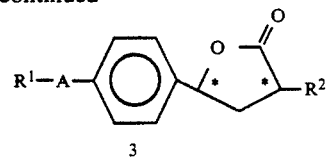
3 wherein R¹, —A— and R² are as defined above and X represents a leaving group such as halogen atom, p-toluenesulfonyloxy group, methanesulfonyloxy group, etc.

Namely, by reacting an alkylating agent expressed by R²—X with an optically active γ-butyrolactone 8 in the presence of an alkali such as LDA, it is possible to prepare a diastereomer 3. As to 3, by subjecting it to diastereomer separation as described above, it is possible to prepare compound (I) of trans-form and cis-form.

Herein, the compound 8 used as the raw material may be preferably prepared according to the following method:

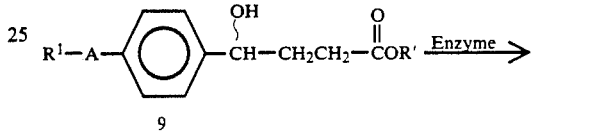
9

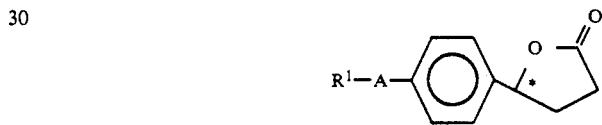
8 wherein R¹, —A— and R' are as defined above.

Namely, an enzyme is reacted with a racemic hydroxy ester 9 to obtain an optically active lactone 8 and an optically active hydroxy ester 9 having an absolute configuration opposite to that of 8.

When 9 is cyclized under an acidic condition, a lactone having an absolute configuration opposite to that of 8 is obtained.

As enzymes effective for this enzymatic reaction, there are Poroine pancreatic lipase (hereinafter abbreviated to PPL), etc.

Further, as shown in the following equations:

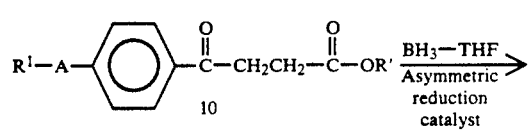
10

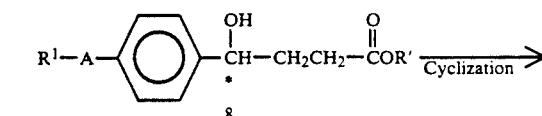
8

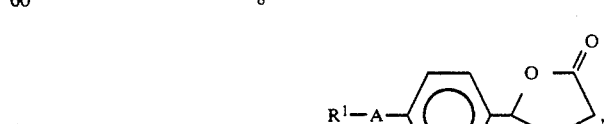
8 a borane-THF complex is reacted with a γ-keto ester 10 in the presence of an asymmetric reduction catalyst (representative examples: β-methyloxazaborolidine, β-phenyloxazaborolidine, β-butyloxazaborolidine, etc.) (reference literatures: D. J. Masley et al., J. Org. Chem., 56, 751-762 (1991), E. J. Colley et al., J. Am. Chem. Soc., 109, 7925-7926 (1987)), to subject the compound 10 to asymmetric reduction, thereby high-stereoselectively preparing a hydroxy ester 9, followed by cyclizing the compound 9 to obtain an optically active lactone 8.

FUNCTION AND EFFECTIVENESS OF THE INVENTION

The first function and effect of the compound of the present invention consist in that when the compound is added to a basic substance for achiral, ferroelectric liquid crystal compositions, the spontaneous polarization value of the resulting composition increases notably. As described later in Examples in more detail, the spontaneous polarization value amounts to about twice those of already reported compounds having a phenyl group linked to the α-position thereof. This property results directly in making the response rate of ferroelectric liquid crystal compositions higher. When an optically active compound is added to a compound or a composition as a basic substance, exhibiting Sc phase or the like related to superior display characteristic for moving picture display, etc., thereby inducing ferroelectricity, the added optically active compound is desired to exhibit a large spontaneous polarization value and yet a low viscosity. The present invention is well provided with these characteristics.

Further, as described above in the Summary of the Invention the second function and effect of the present invention consist in that the compound of the present invention is lower in viscosity than so far reported compounds; hence the compound can further contribute to making the response rate of ferroelectric liquid crystal compositions higher.

As described later in Examples in more detail, when the compound of the present invention is compared with the highest response rate compound Ic (abbreviated to compound B) reported in preprints of the 15th Japan Liquid Crystal Symposium, 1A11, p. 34, the response time in the present invention is shortened, whereby the effect of removing the linking group from the lactone compound is clearly shown.

Further, since the optically active compound of the present invention has optically active carbon atoms, when the compound is added to nematic liquid crystals, it has a capability of inducing twisted structure. As nematic liquid crystals having twisted structure, i.e. chiral nematic liquid crystals, do not form the so-called reverse domain of TN mode display elements, the compound of the present invention can be utilized as an agent for preventing the reverse domain from forming.

The compound of the present invention will be described in more detail by way of Examples.

The measurement methods of various physical properties of ferroelectric liquid crystals were carried out as follows:

(1) Spontaneous polarization (Ps): according to triangle wave method.

(2) Tilt angle (θ): evaluated in terms of ½ the moving angle between a distinction position obtained when a sufficiently high electric field of the critical voltage or higher was impressed to a homogeneously aligned cell, and a distinction position at the time of polarity reversion.

(3) Response time (τ): evaluated in terms of time in change of the intensity of transmitted light, obtained a composition was filled in a cell of 2 μm thickness with transparent electrodes having polyvinyl alcohol coated thereon, followed by rubbing the surface to subject it to a parallel aligning treatment, and a square wave of ±10 V/μm and 100 Hz were impressed.

(4) Viscosity (η): calculated from a full width at half-maximum of the polarization switching current upon field reversal, and the spontaneous polarization (H. Takezoe et al., Japan Journal of Applied Physics, 26, L255 (1987).

Further, since Ps and η depend greatly upon θ, in order to prevent the measurement values from depending upon θ, there are introduced normalized values of Po and ηo, each defined by Po=P/sinθ and ηo=η/sin²θ, respectively.

EXAMPLE 1

Rel-(αS,γS)-α-hexyl-γ-(4-heptyloxyphenyl)-γ-butyrolactone and rel-(αR,γS)-α-hexyl-γ-(4-heptyloxyphenyl)-γ-butyrolactone (Compound No. 39) (hereinafter, "rel" shows that the absolute configuration is unclear, but the relative configuration is clarified)

(Preparation of a compound of the formula (I) wherein $R^1$=heptyloxy, $R^2$=hexyl and —A—=single bond)

The First Step

Preparation of 3-(4-heptyloxybenzoyl)propionic acid

Succinic anhydride (62.4 g) mashed by a mortar and pestle was placed in a 1 l three-necked flask, followed by adding heptyloxybenzene (100 g) and nitrobenzene (300 ml), portion-wise adding anhydrous aluminum chloride (150 g) under ice cooling, heating the mixture up to 50° C., agitating for 2 hours, allowing to stand overnight, after which the resulting reaction solution was poured in water, and subjected to steam distillation to distil off excess nitrobenzene, followed by ice-cooling, filtering off the resulting solids, heating under reflux together with toluene to remove water by means of Dien-Stark type drain tube, filtering off the solution while hot, recrystallizing from the filtrate, and further filtering off the resulting crystals, to obtain 3-(4-heptyloxybenzoyl)propionic acid (114.5 g). m.p.: 103.5°–105.7° C.

The Second Step

Preparation of ethyl 3-(4-heptyloxybenzoyl)propionate 3-(4-Heptyloxybenzoyl)propionic acid (50 g) and ethanol (1 l) were added into a 3 l three-necked flask, followed by gradually adding conc. sulfuric acid (50 ml), heating the mixture under reflux for 8 hours, distilling off ethanol (500 ml), pouring the reaction solution in a mixture of ice water (1 l) and toluene (1 l), washing the resulting organic layer with water, 2N—NaOH solution and saturated NaCl aqueous solution in this order, drying the organic layer over anhydrous magnesium sulfate, concentrating the organic layer under reduced pressure, and recrystallizing the resulting concentrate from ethanol to obtain colorless, crystalline ethyl 3-(4-heptyloxybenzoyl)propionate (60 g). m.p.: 39.7°–40.1° C.

The Third Step butanoate

Ethyl 3-(4-heptyloxybenzoyl)propionate (30 g), diethyl ether (250 ml) and methanol (250 ml) were placed in a 2 l three-necked flask, followed by adding a solution of sodium borohydride (1.8 g) dissolved in distilled water (6 ml), under ice cooling, agitating the solution as it was, at 0° C. for 2 hours, allowing to stand at −10° C. overnight, adding to the reaction solution, diethyl ether (300 ml) and saturated NaHCO$_3$ aqueous solution (300 ml), washing the resulting organic layer with water until the washing water became neutral, drying over anhydrous magnesium sulfate and concentrating the organic layer under reduced pressure to obtain colorless, syrup-like ethyl 4-(4-heptyloxyphenyl)-4-hydroxybutanoate (25 g).

The Fourth Step
Preparation of rel-(S)-γ-(4-heptyloxyphenyl)-γ-butyrolactone Ethyl 4-(4-heptyloxyphenyl)-4-hydroxybutanoate (17 g), porcine pancreatic lipase (hereinafter abbreviated to PPL) (34.4 g) and anhydrous diethyl ether (500 ml) were placed in a 1 l three-necked flask( followed by agitating the mixture at room temperature for 4 days, filtering off PPL, concentrating the filtrate under reduced pressure, and purifying the concentrate according to chromatography, to obtain rel-(S)-γ-(4-heptyloxyphenyl)-γ-butyrolactone (4 g) (69% e.e., optical purity (%) was measured by Chiral Cell OB made by Daisel Co., Ltd., e.e.: abbreviation of enantiomer excess, hereinunder this applies to) and ethyl rel-(R)-γ-(4-heptyloxyphenyl)hydroxybutanoate (5.2 g) ($[\alpha]_D^{26.0}$−13.69 (c 10.24, chloroform)). The former was recrystallized from ethanol, followed by removing the resulting crystals, concentrating the mother liquor under reduced pressure and recrystallizing the concentrate from ethanol to obtain rel-(S)-γ-(4-heptyloxyphenyl)-γ-butyrolactone (3.8 g) (95% e.e.). m.p.: 44.0° C., $[\alpha]_D^{31.6}$+6.62 (c 11.89, chloroform).

$^1$H-NMR: δ (ppm) TMS internal standard: 0.90 (t, 6 H), 1.10∼2.60 (m, 24 H), 3.95 (t, 2 H), 6.90∼7.20 (q, 4 H).

The Fifth Step
Preparation of rel-(αS,γS)-α-hexyl-γ-(4-heptyloxyphenyl)-γ-butyrolactone and rel-(αR,γS)-α-hexyl-γ-(4-heptyloxyphenyl)-γ-butyrolactone Rel-(S)-γ-(4-heptyloxyphenyl)-γ-butyrolactone (3.0 g) and anhydrous tetrahydrofuran (50 ml) were placed in a 200 ml three-necked flask, followed by cooling the mixture down to −65° C. with stirring, dropwise adding a tetrahydrofuran solution of lithium diisopropylamide (21.8 mmol) (hereinafter abbreviated to LDA) over 30 minutes, cooling down to −65° C. with stirring for one hour, dropwise adding a mixed solution of hexylbromide (2.71 g), hexamethylphosphoric triamide (hereinafter abbreviated to HMPA) (2.93 g) and anhydrous tetrahydrofuran (5 ml) over 20 minutes, gradually raising the temperature, agitating the mixture at room temperature overnight, adding ice water (50 ml) and toluene (200 ml), washing the resulting organic layer with 2N-hydrochloric acid, saturated NaHCO$_3$ aqueous solution and saturated NaCl aqueous solution in this order, drying the organic layer over anhydrous magnesium sulfate, removing magnesium sulfate, concentrating the organic layer under reduced pressure, separation-purifying according to chromatography and recrystallizing from ethanol, to obtain rel-(αS,γS)-α-hexyl-γ-(4-heptyloxyphenyl)-γ-butyrolactone (cis-form) (0.05 g). m.p.: 74.8°–75.8° C.

$^1$H-NMR: δ (ppm) TMS internal standard: 0.90 (t, 6 H), 1.10∼2.60 (m, 24 H), 3.95 (t, 2 H), 5.30 (dd, 1 H), 6.90∼7.20 (q, 4 H).

Further, a diastereomer obtained by the same separation-purification according to chromatography was recrystallized from ethanol to obtain rel-(αS,γR)-α-hexyl-γ-(4-heptyloxyphenyl)-γ-butyrolactone (trans-form) (0.1 g). m.p.: 45.9°–47.0° C.

$[\alpha]_D^{32.8}$−6.78 (c 1.032, chloroform) $^1$H-NMR: δ (ppm) TMS internal standard: 0.90 (t, 6 H), 1.00∼2.60 (m, 24 H), 3.95 (t, 2 H), 5.45 (dd, 1 H), 6.90∼7.20 (q, 4H).

REFERENCE EXAMPLE 1

Preparation of (αS,γR)-α-(4-butylphenyl)-γ-hexyl-γ-butyrolactone and (αR,γR)-α-(4-butylphenyl)-γ-hexyl-γ-butyrolactone
(each, a compound having phenyl group linked to α-position of lactone ring)

4-Butylphenylacetic acid (5 g) was dissolved in THF (100 ml), followed by cooling the solution down to −60° C., dropwise adding a tetrahydrofuran solution of LDA (10.4 mmol) over 30 minutes, raising the temperature up to 0° C., agitating for 30 minutes, cooling down to −60° C., dropwise adding a mixed solution of (R)-1,2-epoxyoctane (3.4 g) with anhydrous THF (5 ml) over 10 minutes, gradually raising the temperature, agitating at room temperature overnight, pouring the reaction solution in ice water (100 ml) and toluene (200 ml), washing the resulting organic layer with 6N—HCl, 2N—NaOH and saturated NaCl aqueous solution in this order, drying over anhydrous magnesium sulfate, concentrating the organic layer under reduced pressure, placing the resulting concentrate in a 1 l three-necked flask, adding toluene (250 ml) and p-toluenesulfonic acid (1.1 g), heating the mixture under reflux for 4 hours, dehydrating with a Dien-Stark type drain tube, adding ice water (100 ml), washing the organic layer with 6N—HCl, 2N—NaOH and saturated NaCl aqueous solution in this order, drying over magnesium sulfate, concentrating the organic layer under reduced pressure, separation-purifying according to chromatography and recrystallizing from ethanol to obtain (αS,γR)-α-(4-butylphenyl)-γ-hexyl-γ-butyrolactone (trans-form) (0.8 g). m.p.: 37.7° C.

$[\alpha]_D^{29.4}$+30.95 (c 2.142, Chloroform)

$^1$H-NMR: δ (ppm) TMS internal standard: 1.10∼2.80 (m, 18 H), 3.95 (dd, 1 H), 4.60 (m, 1 H), 7.10 (s, 4 H).

According to the same chromatography as in Example 1, (αR,γR)-γ-(4-butylphenyl)-γ-hexyl-γ-butyrolactone (cis-form) (0.27 g). m.p.: 61.5° C.

$[\alpha]_D^{30.8}$+11.76 (c 1.088, Chloroform)

$^1$H-NMR: δ (ppm) TMS internal standard: 0.90 (t, 6 H), 1.10∼2.80 (m, 18 H), 3.85 (dd, 1 H), 4.45 (m, 1 H), 7.15 (s, 4 H).

EXAMPLE 2

Preparation of
rel-(αS,γS)-α-hexyl-γ-(4-heptylphenyl)-γ-butyrolactone and
rel-(αR,γS)-α-hexyl-γ-(4-heptylphenyl)-γ-butyrolactone [compound of No. 14 ($R^1$=heptyl, $R^2$=hexyl and —A—=single bond in the formula (I)]

The First Step

Preparation of 3-(4-heptylbenzoyl)propionic acid

The first step of Example 1 was repeated except that succinic anhydride (62.4 g) was replaced by 68.1 g thereof and heptyloxybenzene (100 g) was replaced by heptylbenzene (100 g), to obtain 3-(4-heptylbenzoyl)propionic acid (110 g). m.p.: 101.0°–103.5° C.

The Second Step

Preparation of ethyl 3-(4-heptylbenzoyl)propionate

Using the total quantity of 3-(4-heptylbenzoyl)propionic acid obtained above, and in the same manner as in the second step of Example 1, colorless syrup-form ethyl 3-(4-heptylbenzoyl)propionate (110 g) was obtained.

The Third Step

Preparation of ethyl 4-(4-heptylphenyl)-4-hydroxybutanoate

Using ethyl 3-(4-heptylbenzoyl)propionate (60 g) obtained above and in the same manner as in the third step of Example 1, colorless, syrup-form ethyl 4-(4-heptylphenyl)-4-hydroxybutanoate (24.6 g) was obtained.

The Fourth Step

Preparation of rel-(S)-γ-(4-heptylphenyl)-γ-butyrolactone

Using ethyl 4-(4-heptylphenyl)-4-hydroxybutanoate obtained above (12 g) and in the same manner as in the fourth step of Example 1, colorless, syrup-form rel-(S)-γ-(4-heptylphenyl)-γ-butyrolactone (69.9% e.e.) (2.57 g) was obtained.

$[\alpha]_D^{24.6}$7.21 (c 10.612 Chloroform)

$^1$H-NMR: δ (ppm) TMS internal standard: 0.90 (m, 3 H) 1.10~1.80 (m, 24 H), 2.40~2.90 (m, 2 H), 5.50 (dd, 1 H), 7.20 (s, 4 H).

The Fifth Step

Preparation of rel-(αS,γS)-α-hexyl-γ-(4-heptylphenyl)-γ-(4-heptylphenyl)-γ-butyrolactone Using rel-(S)-γ-(4-heptylphenyl)-γ-butyrolactone (1 g) and in the same manner as in the fifth step of Example 1, colorless, crystalline rel-(αS,γS)-α-hexyl-γ-(4-heptylphenyl)-γ-butyrolactone (cis-form) (0.4 g). m.p.: 68.9°–71.0° C.

$H^1$-NMR: δ (ppm) TMS internal standard: 0.90 (m, 6 H), 1.10~2.20 (m, 22 H), 2.40~3.00 (m, 3 H), 5.30 (dd, 1 H), 7.20 (s, 4 H).

Further, in the same manner, colorless, crystalline rel-(αR,γS)-α-hexyl-γ-(4-heptylphenyl)-γ-butyrolactone (trans-form) (0.4 g) was obtained. m.p.: 45.9°–48.0° C.

$^1$H-NMR: 6 (ppm) TMS internal standard: 0.90 (m, 6 H), 1:10~2.20 (m, 22 H), 2.40~3.00 (m, 3 H), 5.50 (t, 1 H), 7.20 (s, 4 H).

EXAMPLE 3

Preparation of
rel-(αS,γS)-α-hexyl-γ-(4'-pentylbiphenyl-4-yl)-γ-butyrolacone and
rel-(αR,γS)-α-hexyl-γ-(4'-pentylbiphenyl-4-yl)-γ-butyrolactone (compound of No. 62) (in the formula (I), $R^1$=pentyl, $R^2$=hexyl and —A—=

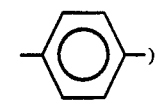

The First Step

Preparation of 3-(4-(4'-pentylphenyl)benzoyl)propionic acid

The first step of Example 1 was repeated except that heptyloxybenzene was replaced by 4-pentylbiphenyl, to carry out Friedel-Crafts reaction, thereby obtaining colorless, crystalline 3-(4-(4'-pentylphenyl)benzoyl)propionic acid (116 g). m.p.: 179.2°–183° C.

The Second Step

Preparation of ethyl 3-(4-(4'-pentylphenyl)benzoyl)propionate

Using 3-(4-(4'-pentylphenyl)benzoyl)propionic acid (116 g) obtained above and by esterifying in the same manner as in the second step of Example 1, colorless, crystalline ethyl 3-(4-(4'-pentylphenyl)benzoyl)propionate (88.7 g) was obtained. m.p.: 110.8°–112.6° C.

The Third Step

Preparation of ethyl 4-(4'-pentylbiphenyl-4-yl)-4-hydroxybutanoate

Using ethyl 3-(4-(4'-pentylphenyl)benzoyl)propionate (50 g) obtained above and by carrying out reduction in the same manner as in the third step of Example 1, oily ethyl 4-(4'-pentylbiphenyl-4-yl)-4-hydroxybutanoate (30 g).

The Fourth Step

Preparation of rel-(S)-γ-(4'-pentylbiphenyl-4-yl)-γ-butyrolactone

Using ethyl 4-(4'-pentylbiphenyl-4-yl)-4-hydroxybutanoate (30 g) obtained above and by carrying out an enzymatic reaction same as in the fourth step of Example 1, colorless, crystalline rel-(S)-γ-(4'-pentylbiphenyl-4-yl)-γ-butyrolactone (69.6% e.e.*) (6.58 g) was obtained. m.p.: 98.8° C.

*: Measurement of optical purity:

$[\alpha]_D^{32.0}$+12.53 (c 11.381, Chloroform)

$^1$H-NMR: δ (ppm) TMS internal standard: 0.90 (t, 3 H), 1.20~2.00 (m, 8 H), 2.40~3.00 (m, 4 H), 5.60 (t, 1 H), 7.20~8.20 (m, 8 H).

An optically active lactone was firstly reduced by lithium aluminum hydride into a diol compound, followed by reacting it with (R)-(+)-α-methoxy-α-(trifluoromethyl)phenylacetic acid to obtain a diester compound, and carrying out H.P.L.C. measurement using a reverse phase ODS column, to determine the optical purity. This applies to the subsequent cases.

The Fifth Step

Preparation of rel-(αS,γS)-α-hexyl-γ-(4'-pentylbiphenyl-4-yl)-γ-butyrolactone and rel-(αR,γS)-α-hexyl-γ-(4'-pentylbiphenyl-4-yl)-γ-butyrolactone Using rel-(S)-γ-(4'-pentylbiphenyl-4-yl)-γ-butyrolactone (0.5 g) obtained above and by alkylating in the same manner as in the fifth step of Example 1, colorless, crystalline rel-(αS,γS)-α-hexyl-γ-(4'-pentylbiphenyl-4-yl)-γ-butyrolactone (cis-form) (0.05 g) was obtained.

$^1$H-NMR: δ (ppm) TMS internal standard: 0.90 (m, 6 H), 1.20~2.20 (m, 20 H), 2.40~3.00 (m, 3 H), 5.40 (dd, 1 H), 7.20~7.80 (m, 8 H).

Further, in the same manner as above, colorless, crystalline rel-(αR,γS)-α-hexyl-γ-(4'-pentylbiphenyl-4-yl)-γ-butyrolactone (trans-form) (0.05 g) was obtained.

$^1$H-NMR: δ (ppm) TMS internal standard: 0.90 (m, 6 H), 1.20~2.00 (m, 20 H), 2.40~3.00 (m, 3 H), 5.60 (t, 1 H), 7.20~7.80 (m, 8 H).

EXAMPLE 4

Preparation of rel-(αS,γS)-α-pentyl-γ-(4'-pentylbiphenyl-4-yl)-γ-butyrolactone and rel-(αR,γS)-α-pentyl-γ-(4'-pentylbiphenyl-4-yl)-γ-butyrolactone (compound of No. 57) (in the formula (I), R$^1$=pentyl, R$^2$=pentyl and —A—=

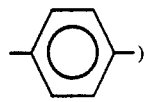

The First Step

Preparation of ethyl rel-(S)-γ-(4'-pentylbiphenyl-4-yl)-4-hydroxybutanoate

Ethyl 3-(4-(4'-pentylphenyl)benzyl)propionate (15 g) obtained in the second step of Example 3, (S)-tetrahydro-1-methyl-3,3-diphenyl-1H,3H-pyrrolo[1,2-C][1,3,2]oxazaborole (0.59 mol/l toluene solution) (3.73 ml) and anhydrous THF (40 ml) were placed in a 100 ml three-necked flask, followed by agitating the mixture, dropwise adding a borane THF solution (1.0 mol/l) (26.4 ml) under ice cooling over one hour, thereafter agitating the mixture at room temperature for 30 minutes, adding MeOH (6 ml), saturated NaCl aqueous solution (6 ml) and 1N—HCl (0.75 ml), further adding toluene (100 ml), washing the resulting organic layer with water, drying over anhydrous magnesium sulfate, removing magnesium sulfate, concentrating the organic layer under reduced pressure and separation-purifying the concentrate according to chromatography, to obtain ethyl rel-(S)-γ-(4'-pentylbiphenyl-4-yl)-4hydroxybutanoate (9.88 g).

The Second Step

Preparation of rel-(S)-γ-(4'-pentylbiphenyl-4-yl)-γ-butyrolactone

The total quantity of ethyl rel-(S)-γ-(4'-pentylbiphenyl-4-yl)-4-hydroxybutanoate obtained above was placed in a 100 ml three-necked flask, followed by adding anhydrous THF (15 ml), dissolving it with stirring, adding sodium hydride (0.02 g) at room temperature, agitating the mixture for 45 minutes, adding 6N—HCl (15 ml) and ethyl acetate (50 ml), washing the resulting organic layer with water, drying it over anhydrous magnesium sulfate, removing magnesium sulfate, concentrating the organic layer under reduced pressure and recrystallizing from alcohol, to obtain rel-(S)-γ-(4'-pentylbiphenyl-4-yl)-γ-butyrolactone (96.78% e.e.) (3.2 g). m.p.: 98.2°–100.7° C.

[α]$_D^{26.0}$+16.51 (c 10.649, Chloroform)

$^1$H-NMR: δ (ppm) TMS internal standard: 0.90 (m, 3 H), 1.20~2.00 (m, 8 H), 2.00~2.80 (m, 4 H), 5.60 (t, 1 H), 7.20~8.20 (m, 8 H).

The Third Step

Preparation of rel-(αS,γS)-α-pentyl-γ-(4'-pentylbiphenyl-4-yl)-γ-butyrolactone and rel-(αR,γS)-α-pentyl-γ-(4'-pentylbiphenyl-4-yl)-γ-butyrolactone Using rel-(S)-γ-(4'-pentylbiphenyl-4-yl)-γ-butyrolactone (1 g) obtained above and in the same manner as in the fifth step of Example 1, colorless, crystalline rel-(αS,γS)-α-pentyl-γ-(4'-pentylbiphenyl-4-yl)-γ-butyrolactone (cis-form) (0.25 g) was obtained. m.p.: 109.4°–111.9° C.

$^1$H-NMR: 67 (ppm) TMS internal standard: 0.90 (m, 6 H), 1.20~2.20 (m, 15 H), 2.40~3.00 (m, 4 H), 5.60 (t, 1 H), 7.20~7.70 (m, 8 H).

Further, in the same manner, colorless, crystalline rel-(αR,γS)-α-pentyl-γ-(4'-pentylbiphenyl-4-yl)-γ-butyrolactone (trans-form) (0.25 g) was obtained. m.p. 86.2°–88.4° C.

$^1$H-NMR: δ (ppm) TMS internal standard: 0.90 (m, 6 H), 1.20~2.20 (m, 15 H), 2.40~3.00 (m, 4 H), 5.39 (dd, 1 H), 7.20~7.70 (m, 8 H).

EXAMPLE 5

Preparation of rel-(αS,γS)-α-octyl-γ-(4'-pentylbiphenyl-4-yl)-γ-butyrolactone and rel-(αR,γS)-α-octyl-γ-(4'-pentylbiphenyl-4-yl)-γ-butyrolactone (compound of No. 72) (in the formula (I), R$^1$=pentyl, R$^2$=octyl and —A—=

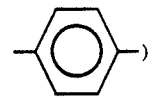

Using rel-(S)-γ-(4'-pentylbiphenyl-4-yl)-γ-butyrolactone (1 g) obtained in the second step of Example 4, and by alkylating in the same manner as in the fifth step of Example 1, colorless, crystalline rel-(αS,γS)-α-octyl-γ-(4'-pentylbiphenyl-4-yl)-γ-butyrolactone (cis-form) (0.25 g) was obtained. m.p.: 114.0°–117.7° C.

$^1$H-NMR: δ (ppm) TMS internal standard: 0.90 (m, 6 H), 1.20~2.20 (m, 21 H), 2.50~3.00 (m, 4 H), 5.39 (dd, 1 H), 7.20~7.70 (m, 8 H).

Further, in the same manner as above, colorless, crystalline rel-(αR,γS)-a-octyl-γ-(4'-pentylbiphenyl-4-yl)-γ-butyrolactone (trans-form) (0.25 g) was obtained. m.p.: 89.5°–91.0° C.

$^1$H-NMR: δ (ppm) TMS internal standard: 0.90 (m, 6 H), 1.20~2.20 (m, 21 H), 2.50~3.00 (m, 4 H), 7.20~7.70 (m, 8 H).

EXAMPLE 6

Preparation of rel-(αS,γS)-α-(hexyl)-γ-4-(4'-pentylcyclohexyl)-phenyl)-γ-butyrolactone and rel-(αR,γS)-α-(hexyl)-γ-(4-(4'-pentylcyclohexyl)-phenyl)-γ-butyrolactone (compound of No. 112) (in the formula (I), $R^1$=pentyl, $R^2$=hexyl and —A—=1,4-cyclohexylene)

The First Step

Preparation of 3-(4-(4'-pentylcyclohexyl)benzoyl)propionic acid

Friedel-Crafts reaction was carried out in the same manner as in the first step of Example 1 to obtain 3-(4-(4'-pentylcyclohexyl)benzoyl)propionic acid was obtained.

The Second Step

Preparation of ethyl 3-(4-(4'-pentylcyclohexyl)benzoyl)propionate

Using 3-(4-(4'-pentylcyclohexyl)benzoyl)propionic acid obtained above and by esterifying in the same manner as in the second step of Example 1, ethyl 3(4-(4'-pentylcyclohexyl)benzoyl)propionate was obtained.

The Third Step

Preparation of ethyl rel-(S)-γ-(4-(4'-pentylcyclohexyl)phenyl)-4-hydroxybutanoate Using ethyl 3-(4-(4'-pentylcyclohexyl)benzoyl)propionate obtained above and by asymmetric reduction in the same manner as in the first step of Example 4, ethyl rel-(S)-γ-(4-(4'-pentylcyclohexyl)phenyl-4-hydroxybutanoate was obtained.

The Fourth Step

Preparation of rel-(S)-γ-(4-(4'pentylcyclohexyl)phenyl)-γ-butyrolactone

Using ethyl rel-(S)-γ-(4-(4'-pentylcyclohexyl)-phenyl)-4-hydroxybutanoate obtained above and by cyclizing in the same manner as in the second step of Example 4, colorless, crystalline rel-(S)-γ-(4-(4'-pentylcyclohexyl)phenyl)-γ-butyrolactone was obtained.

$[\alpha]_D^{28.0}$ +9.10 (c 10.916, CHCl$_3$)

$^1$H-NMR: δ (ppm) TMS internal standard: 0.90 (m, 3 H), 1.20~3.00 (m, 25 H), 5.47 (t, 1 H), 7.20 (s, 4 H).

The Fifth Step

Preparation of rel-(αS,γS)-γ-hexyl-γ-(4-(4'-pentylcyclohexyl)phenyl)-γ-butyrolactone and rel-(αR,γS)-α-hexyl-γ-(4-(4'-pentylcyclohexyl)phenyl)-γ-butyrolactone Using rel-(S)-γ-(4-(4'-pentylcyclohexyl)phenyl)-γ-butyrolactone obtained above and in the same manner as in the fifth step of Example 1, rel-(αS,γS)-α-hexyl-γ-(4-(4'-pentylcyclohexyl)phenyl)-γ-butyrolactone (cis-form) and rel-(αR,γS)-α-hexyl-γ-(4-(4'-pentylcyclohexyl)phenyl)-γ-butyrolactone (trans-form) were obtained.

EXAMPLE 8 (USE EXAMPLE 1)

A liquid crystal composition A consisting of

| | |
|---|---|
| 5-octyl-2-(4-hexyloxyphenyl)pyrimidine | 30 wt. % |
| 5-octyl-2-(4-octyloxyphenyl)pyrimidine | 20 wt. % |
| 5-octyl-2-(4-nonyloxyphenyl)pyrimidine | 10 wt. % |
| 5-octyl-2-(4-decyloxyphenyl)pyrimidine | 10 wt. % |
| 5-octyl-2-(4-pentyl-4-biphenylyl)pyrimidine | 20 wt. % and |
| 5-octyl-2-(4'-heptyl-4-biphenylyl)pyrimidine | 10 wt. %, | exhibits the following phase transition points:
Cr . 4° C., Sc . 65° C., Sa . 79° C., N . 90° C., I A mixture (composition B) of this composition A (95 wt. %) with cis-rel-(αS,γS)-α-hexyl-γ-4 -heptyloxyphenyl)-γ-butyrolactone (the cis-form compound of Example 1) (5 wt. %) exhibited the following phase transition points:
Cr~Sc* . 56° C., Sa . 68.6° C., N* . 77.4° C., I The values of ferroelectric liquid crystal physical properties at 40° C. of the composition B were as follows:

| | |
|---|---|
| Ps | 9.1 (nC/cm$^2$) |
| Tilt angle | 17.7 (°) |
| Response time | 27.2 (μsec) |
| Po | 29.9 (nC/cm$^2$) |
| η0 | 93.0 (mPa * sec) |

REFERENCE EXAMPLE 2

A mixture (composition C) of the composition A (95 wt. %) with cis-rel-(αR,γR)-α-(4-butylphenyl)-γ-hexyl-γ-butyrolactone (cis-form compound of Reference example 1) (5 wt. %) exhibited the following phase transition points:
Cr~Sc* . 47.6° C., Sa 58.5° C., N* . 75.1° C., I The values of ferroelectric liquid crystal physical properties at 40° C. of the composition C were as follows:

| | |
|---|---|
| Ps | 2.0 (nC/cm$^2$) |
| Tilt angle | 14.4 (°) |
| Response time | 56 (μsec) |
| P$_0$ | 8.0 (nC/cm$^2$) |
| η0 | 53.4 (mPa * sec) |

As seen from the above results, the ferroelectric properties greatly vary depending upon the difference in the directional properties of lactone ring, and the lactone of the compound of the present invention is superior.

EXAMPLE 9 (USE EXAMPLE 2)

A mixture (composition D) of the composition A (98 wt. %) with cis-rel-(αS,γS)-α-hexyl-γ-(4-heptyloxyphenyl)-γ-butyrolactone (cis-form compound of Example 1) (2 wt. %) exhibited the following phase transition points:
Cr~Sc* . 56° C., Sa 68.6° C., N* . 77.4° C., I The values of the ferroelectric liquid crystal physical properties at 25° C. of the composition D were as follows:

| | |
|---|---|
| Ps | 4.5 (nC/cm$^2$) |
| Tilt angle | 21.7 (°) |
| Response time | 64 (μsec) |
| P$_0$ | 12.2 (nC/cm$^2$) |
| η0 | 77.5 (mPa * sec) |

REFERENCE EXAMPLE 3

A mixture (composition E) of an achiral base liquid crystal of phenylpyrimidine group BSCO22 described in preprint of the 15th Japan Liquid Crystal Symposium, 1A11 (98 wt. %) with cis-form of compound B (No. 1c) (2 wt. %) has been described to exhibit the following phase transition points:

Cr~Sc* . 46° C., Sa . 68° C., N* . 70° C., I

Further, the values of the ferroelectric liquid crystal physical properties at 40° C. of the composition E has been described to be as follows:

| Ps | 4 (nC/cm$^2$) |
|---|---|
| Tilt angle | 10 (°) |
| Response time | 77 (μsec) |
| P$_0$ | 230 (nC/cm$^2$) |

The $\eta_0$ of the composition E cannot be calculated, but it is seen from the relationship among P$_0$, $\theta$ and response time that its viscosity is high.

EXAMPLE 10 (USE EXAMPLE 3)

A nematic liquid crystal composition consisting of

| 4'-ethyl-4-cyanobiphenyl | 20 wt. % |
|---|---|
| 4'-pentyl-4-cyanobiphenyl | 35 wt. % |
| 4'-octyl-4-cyanobiphenyl | 30 wt. % and |
| 4''-pentyl-4-cyanoterphenyl | 15 wt. %, | was filled as a sample, in a cell of 10 μm thick, provided with transparent electrodes obtained by coating polyvinyl alcohol as an agent for aligning treatment and rubbing the surface to subject it to a parallel aligning treatment to construct a TN mode liquid crystal display element. When this element was observed under a polarizing microscope, a reverse twist domain was observed. To this composition was added 0.1 wt. % of trans-rel-(αS,γS)-α-hexyl-γ-(4-heptyloxyphenyl)-γ-butyrolactone (trans-form compound of Example 1). When the resulting nematic liquid crystal composition was similarly observed, no reverse twist domain was observed, and a uniform nematic phase was observed.

EXAMPLE 11 (USE EXAMPLE 4)

To a nematic liquid crystal composition ZLI-1132 made by Merck Co., Ltd. was added 0.1 wt. % of cis-rel-(αS,γS)-α-hexyl-γ-(4-heptyloxyphenyl)-γ-butyrolactone (cis-form compound of Example 1). The resulting chiral nematic liquid crystal composition exhibited the following chiral pitches:

| Temperature (° C.) | Pitch length (μm) |
|---|---|
| 60 | 16.0 |
| 50 | 15.6 |
| 40 | 15.6 |
| 30 | 16.0 |
| 20 | 16.8 |

As seen from the above results, the compound of the present invention has a short chiral pitch length induced; hence it is most suitable to the mode requiring a strong twist force as in the case of STN, etc. Further, as the chiral pitch length does not vary so much, depending upon temperature and it is almost uniform, it is possible to prepare a display element having a small temperature dependency.

What we claim is:

1. A lactone compound expressed by the formula

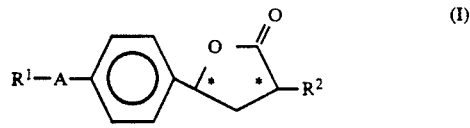

(I)

wherein R$^1$ represents a linear or branched alkyl group or alkoxy group of 1 to 15 carbon atoms, R$^2$ represents a linear or branched alkyl group of 1 to 16 carbon atoms, —A— represents a single bond, a 1,4-phenylene group or a 1,4-cyclohexylene group and * represents an asymmetric carbon atom.

2. The lactone compound according to claim 1, wherein —A— represents a single bond.

3. The lactone compound according to claim 1, wherein —A— represents a 1,4-phenylene group.

4. The lactone compound according to claim 1, wherein —A— represents a 1,4-cyclohexylene group.

5. The lactone compound according to claim 1, wherein R$^1$ represents a linear or branched alkyl group of 1 to 15 carbon atoms.

6. The lactone compound according to claim 1, wherein R$^1$ represents a linear or branched alkoxy group of 1 to 15 carbon atoms.

7. A liquid crystal composition comprising at least two components at least one of which is a lactone compound of the formula (I) as set forth in claim 1.

8. A liquid crystal element which comprises a ferroelectric liquid crystal composition comprising at least two components at least one of which is a lactone compound of the formula (I) as set forth in claim 1.

* * * * *